(12) United States Patent
Choate (10) Patent No.: US 11,567,584 B2
(45) Date of Patent: Jan. 31, 2023

(54) POWERED COMMUNICATION SYSTEM FOR TREATMENT OF CARPAL TUNNEL SYNDROME

(71) Applicant: John I. M. Choate, St. George, UT (US)

(72) Inventor: John I. M. Choate, St. George, UT (US)

(*) Notice: Subject to any disclaimer, the term of this patent is extended or adjusted under 35 U.S.C. 154(b) by 475 days.

(21) Appl. No.: 16/664,287

(22) Filed: Oct. 25, 2019

(65) Prior Publication Data

US 2021/0124427 A1    Apr. 29, 2021

(51) Int. Cl.
| | |
|---|---|
| *G06F 3/02* | (2006.01) |
| *A61B 5/11* | (2006.01) |
| *A61B 5/00* | (2006.01) |
| *A61B 5/0205* | (2006.01) |
| *A61B 5/024* | (2006.01) |

(52) U.S. Cl.
CPC ........ *G06F 3/0219* (2013.01); *A61B 5/02055* (2013.01); *A61B 5/1116* (2013.01); *A61B 5/6897* (2013.01); *A61B 5/7264* (2013.01); *G06F 3/0216* (2013.01); *A61B 5/024* (2013.01)

(58) Field of Classification Search
CPC .... G06F 3/0219; G06F 3/0216; G06F 3/0236; G06F 3/0237; G06F 3/021; A61B 5/02055; A61B 5/1116; A61B 5/6897; A61B 5/7264; A61B 5/024; A61B 5/1124; A61B 2505/09; A61B 5/02416; A61B 5/6826; A61B 5/7267
See application file for complete search history.

(56) References Cited

U.S. PATENT DOCUMENTS

| | | | |
|---|---|---|---|
| 5,352,050 A | 10/1994 | Choate | |
| 5,498,088 A | 3/1996 | Choate | |
| 5,626,429 A | 5/1997 | Choate | |
| 5,718,590 A * | 2/1998 | Choate | ................. G06F 3/0219 434/227 |
| 5,836,705 A * | 11/1998 | Choate | ................. G06F 3/0219 400/486 |
| 6,237,846 B1 * | 5/2001 | Lowell | ................. G06F 3/0216 235/145 R |
| 6,692,435 B1 | 2/2004 | Choate | |
| 7,547,286 B2 | 6/2009 | Choate | |

(Continued)

FOREIGN PATENT DOCUMENTS

WO    2018081416 A1    5/2018

OTHER PUBLICATIONS

International Search Report from PCT Application No. PCT/US2020/057055, dated Feb. 10, 2021.

*Primary Examiner* — Ibrahim A Khan
(74) *Attorney, Agent, or Firm* — Workman Nydegger (57) ABSTRACT

A powered communication system comprises an improved layout of keys configured to treat, mitigate, or delay the onset and reduce the severity of symptoms of carpal tunnel syndrome (CTS) and other pathologies by reducing movement of a user's fingers during typing. A layout of the powered communication system comprises the most-used letters on a home or center row while retaining a plurality of keys in the same placement as the QWERTY keyboard. The powered communication system further comprises customizable function keys to further reduce finger movement and at least one sensor to monitor a user's health while typing.

14 Claims, 4 Drawing Sheets

(56) References Cited

U.S. PATENT DOCUMENTS

| | | | |
|---|---|---|---|
| 10,585,494 B1* | 3/2020 | Porcella | G06F 3/021 |
| 2003/0016985 A1* | 1/2003 | Patel | G06F 3/021 |
| | | | 400/489 |
| 2003/0099497 A1* | 5/2003 | Zhang | G06F 3/0216 |
| | | | 400/472 |
| 2004/0066374 A1* | 4/2004 | Holloway | G06F 3/0238 |
| | | | 345/168 |
| 2004/0168131 A1* | 8/2004 | Blumberg | G06F 3/0237 |
| | | | 715/261 |
| 2005/0062722 A1* | 3/2005 | Hsieh | G06F 3/021 |
| | | | 345/168 |
| 2005/0146505 A1* | 7/2005 | Mandel | B41J 5/10 |
| | | | 345/168 |
| 2006/0114233 A1* | 6/2006 | Radivojevic | G06F 3/0426 |
| | | | 345/168 |
| 2007/0132733 A1* | 6/2007 | Ram | G06F 3/03544 |
| | | | 345/163 |
| 2008/0303698 A1* | 12/2008 | Casparian | G06F 3/0216 |
| | | | 463/47 |
| 2008/0304892 A1 | 12/2008 | Baker | |
| 2009/0223527 A1* | 9/2009 | Choate | G06F 3/0219 |
| | | | 400/489 |
| 2009/0257807 A1* | 10/2009 | Woloschyn | H01H 13/86 |
| | | | 400/489 |
| 2014/0152568 A1 | 6/2014 | Streitz | |
| 2018/0039406 A1* | 2/2018 | Kong | G06F 9/451 |
| 2019/0235638 A1* | 8/2019 | Lee | G06F 3/0235 |
| 2021/0236044 A1* | 8/2021 | Arroyo-Gallego | A61B 5/4023 |

\* cited by examiner

POWERED COMMUNICATION SYSTEM FOR TREATMENT OF CARPAL TUNNEL SYNDROME

FIELD OF THE DISCLOSURE

The disclosure relates to the field of powered medical devices including powered communication systems for treatment of various pathologies.

BACKGROUND

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Communication, including transmitting and receiving information, is essential to a functioning society. Two-handed, eight-finger, two-thumb communication systems including keyboards have become a vital part of everyday life with the proliferation of personal computers and smart devices. The most common keyboard is known as the "QWERTY" keyboard, named after the first six letters that appear from left to right on the topmost row. The QWERTY keyboard has been ubiquitous since its advent with the typewriter keyboard developed by E. Remington & Sons in the $19^{th}$ century. The QWERTY layout was developed to slow the rate at which a user could type by spacing the most-used keys apart (for example on the upper and lower rows), so as to prevent the now-obsolete problem of jamming of the metal arms of the typewriter. The design of the QWERTY keyboard thus requires more extension and flexion of the fingers than is necessary to solve a no-longer-existent problem.

Because it was designed to slow the rate at which a user can type, the QWERTY keyboard suffers from significant disadvantages, including making a user susceptible to pathologies such as carpal tunnel syndrome ("CTS"), the common ailment that results from compression of the median nerve as it passes through the osteofibrous carpal tunnel (defined by the carpal bones and the transverse carpal ligament) along with the tendons of the long digital muscles of the hand. The median nerve can become compressed due to inflammation of the flexor retinaculum, arthritis, or tenosynovitis, among other causes.

Related to, including, or a subset of CTS, are numerous conditions, known by names such as typing disease, repetitive stress injury (RSI), repetitive stress syndrome (RSS), cumulative trauma disease (CTD), cumulative trauma injury (CTI), cumulative trauma disorder, carpal tunnel release, median nerve entrapment, median nerve injury, median neuropathy, musculoskeletal disorder (MSD), nerve compression syndrome, nervous system disease, pathological process, peripheral nervous system disease, peripheral nerve pathology, sprains and strains, tendinitis (also spelled tendonitis), tenosynovitis, upper body fatigue, upper-extremity musculoskeletal disorder (UEMSD), upper extremity mononeuropathy, upper limb mononeuropathy, and other wounds, injuries, and conditions.

CTS and related pathologies can result in paresthesia (tingling), anesthesia (loss of tactile sensation) or hypesthesia (diminished sensation) in the skin of the thumb and fingers. CTS can also result in a progressive loss of strength and coordination of the thumb and fingers. CTS can also result in burning and pain in the thumb and fingers which can radiate up a user's arm toward the shoulder. The symptoms of CTS are cascading, with decreased tactile sensation leading to improper use and increased use of arthritis, among other adverse effects. The effects of CTS can spill over into other fundamental and basic activities of a user's life, including flossing teeth, conducting self-examinations for health purposes, and performing skill-based tasks in a user's job, to name a few. After the onset of the symptoms of CTS, a user is often required to wait until the symptoms naturally decrease in intensity—usually overnight—before returning to normal activities.

CTS affects hundreds of thousands of users in the United States every year, with economic costs in the billions of dollars. Moreover, CTS is likely to continue to grow as a public-health problem as more and more workers around the world work in computer-intensive service and professional careers rather than non- or less-computer-based careers like manufacturing, trades, and agriculture. Use of keyboards will further continue to be relevant even in view of the rise of voice recognition technologies, as many users must continue to type with their hands when they cannot rely upon voice recognition. Such situations may include users who must type words that do not lend themselves well to voice recognition, like computer programming or quantitative and financial-related typing in spreadsheets, or when persons have voices that are obstructed.

While CTS has typically been associated with bent wrists from prolonged periods of computer or other keyboard-related work, it has also been found that repetitive finger flexion is also associated with and contributes to CTS. The QWERTY keyboard requires a user to move their fingers and thumbs in movements that place stress on the carpal tunnel, as the keys are arranged such that a user frequently must utilize the top and bottom rows. Such repetitive finger flexion aggravates existing CTS through hypertrophy of nine flexors and tendons in the hand from excessive moment, leading to slower typing or not typing at all.

Because CTS causes thus constitutes a physical impairment to users, aggressive approaches have been adopted by numerous users and practitioners to alleviate its symptoms. Surgery to relieve CTS is common, as are bracing or splinting, steroid injections, disruptive lifestyle changes, and the use of painkillers such as nonsteroidal anti-inflammatory drugs ("NSAIDs") or in severe cases opioids. The self-evident disadvantages of such treatments—including the risks of surgery, the inconvenience, cost, and disruption of bracing solutions and other lifestyle adjustments, and the side-effects of steroidal injections and painkillers, including risk of addiction and substance abuse—underline the need for an improved medical device such as a powered communication system configured to treat and alleviate the symptoms of CTS.

Painkillers such as NSAIDs are known, for example, to cause chronic kidney disease in certain doses, as well as stomach ulcers and gastrointestinal bleeding, among other side effects and complications. Further, NSAIDs may not be available or suitable for all persons afflicted by CTS, and may cause allergic reactions for some users.

Numerous individuals have attempted to redesign the keyboard from scratch in order to provide an improved layout that requires less movement from a user. Such attempts include the Dvorak and Colemak keyboards. Whereas just 32% of typing is done on the home row of the QWERTY keyboard, 70% and 74% of typing is done on the home row the Dvorak and Colemak keyboards, respectively. Due to the universal market acceptance of the QWERTY keyboard, however, these alternative keyboards have been unable to overcome the inertia of users learning a completely new keyboard. Learning an entirely new keyboard layout requires significant time and effort, especially for older users who have long been accustomed to the QWERTY keyboard, and because of the ubiquitous nature of the QWERTY keyboard which necessitates its continued use in, for example, workplaces, schools, libraries, and etc.

In view of the above, there is a need for an improved powered communication device configured to alleviate, treat, and/or delay the onset of the symptoms of CTS while addressing the difficulty of adopting a new keyboard layout.

SUMMARY

The powered communication system or device of the present disclosure can be in embodiments an interossei lumbricals neuromuscular technology interface therapeutic powered communications system medical device designed to treat persons afflicted with CTS by changing the layout of keys on a keyboard so as to reduce the amount of finger flexion required of a user. The powered communication device of the present disclosure further bridges the divide between existing, failed alternative keyboards such as the Dvorak and Colemak keyboards by retaining elements of the QWERTY layout, so that a user does not have to entirely relearn the layout of keys.

For instance, rather than rearranging a substantial entirety of the keys like Dvorak (in which 24 letters and all five punctuation marks are changed), the powered communication device in embodiments changes 10 letters and two of the punctuation marks. By rearranging a limited number of the keys, the powered communication device of the present disclosure advantageously minimizes the amount of time and effort necessarily involved in re-learning a keyboard while also reducing distance traveled by the user's fingers. This limited and specific rearrangement of the powered communication device of embodiments of the disclosure advantageously results in a re-training time of only eight hours compared to some 54 hours for learning an existing keyboard.

In embodiments of the powered communication device, the most commonly used keys—"t", "h", "e", "o", "r", "d", "i", "n", "a", "l", "s", hereinafter "the ordinals"—are arranged on the middle or home row, reducing the amount of movement including flexion and extension of the fingers and thumbs during typing, while maintaining a substantial number of keys in their pre-existing location in the QWERTY keyboard. Compared to the QWERTY keyboard layout, the powered communication device of embodiments of the present disclosure reduces distance traveled by the fingers by 50% and reduces flexion and extension by 67%.

Motion is also shifted from the elbows to the finger muscles, i.e. the interosseus muscles and the lumbrical muscles. By reducing movement of the fingers and transferring movement from the elbows to the interosseus and lumbrical muscles, contraction and expansion of tendons is reduced, reducing pressure on the median nerve, mitigating and delaying the onset of the symptoms of CTS. The powered communication device of embodiments advantageously extends the time that a user may type before experiencing symptoms of CTS by as much as 60% compared to using the QWERTY keyboard.

Use of the powered communication device of embodiments of the present disclosure advantageously delays or prevents entirely the onset of CTS symptoms, mitigating the need for surgery, bracing, steroids, painkillers, and disruptive lifestyle adjustments.

In embodiments of the powered communication device, the keys can be further rearranged as befitting users typing in languages other than English. For example, Spanish speakers are known to use, in addition to the ordinals, the letter "u" more frequently than English speakers. Accordingly the letter "h" on the home row can be replaced with the letter "u" in certain embodiments to suit users typing in Spanish. Users typing in French likewise may benefit from this arrangement. A button or key of the powered communication device can be provided to manually switch the configuration of the keys between layouts corresponding to particular languages. In embodiments, the individual keys can comprise displays configured to indicate to a user what letter the key represents at a particular time.

In embodiments, the powered communication device further reduces movement of the fingers and thereby delays, treats, and/or mitigates the symptoms of CTS and other pathologies by providing a customization option, wherein the function keys f1-f12 can be set to represent a particular word that is commonly used by a user. By pressing one of the keys f1-f12 so customized, the movement associated with typing each letter of the particular words may be avoided entirely. In embodiments, the powered communication device may comprise a processor configured to automatically determine words commonly typed by a particular user that can advantageously be set to the function keys f1-f12 to further minimize the user's finger movements.

In further embodiments, the powered communication device can comprise a display configured to indicate to a user which word corresponds to each one of the customized function keys f1-f12. The powered communication device may further comprise blank keys that are manually determined by a user, e.g. by self-marking or by programming the key to represent a desired function or character.

The powered communication device can advantageously monitor a user's health, particularly in regards to the symptoms of CTS, by providing individual keys or each of the keys with sensors to monitor, for example, pulse rate and/or body temperature, with information fed to a processor. The processor may determine whether a particular body temperature, pulse rate, combination thereof, or other physical parameter indicates the onset of symptoms of CTS and thereafter indicate to the user to slow down, take a break, change position, or temporarily stop typing. In embodiments, the processor is configured to determine based on factors such as the speed, impact, typing patterns, temperature, and/or pulse rate a user's risk for developing or manifesting the symptoms of CTS, and can determine a treatment recommendation.

Additional features of the powered communication device include, in embodiments, an independent power source, expanded data storage, Bluetooth connectivity, a projector for projection of graphics, a solar power module, a text-recognition key, a voice-recognition key, and others.

The powered communication device of embodiments of the disclosure may further be used in cooperation with a typing-training system. The typing-training system may advantageously comprise a display that shows a sample text to be typed and a plurality of boxes which represent the characters of the powered communication device in a configuration approximating the layouts described herein. The display enables the user to see the location of the character to be typed in sequential order by displaying an emphasis on the box corresponding to the key in the powered communication device.

These and other features, aspects, and advantages of the present disclosure will become better understood regarding the following description, appended claims, and drawings.

BRIEF DESCRIPTION OF THE DRAWINGS

The powered communication device embodiments disclosed in the following drawings are illustrated for example only. The elements and combinations of elements described below and illustrated in the drawings can be arranged and organized differently to result in embodiments still within the spirit and scope of the powered communication device embodiments described herein.

DETAILED DESCRIPTION OF VARIOUS EMBODIMENTS

The powered communication devices of embodiments of the disclosure advantageously delay, treat, or mitigate the onset of symptoms and complications of CTS by arranging the keys of the powered communication device such that the letters most frequently used are arranged on the home row, minimizing the amount of finger movement that a user must make, while leaving many of the keys unmoved from the QWERTY arrangement, such that a user has to expend only minimal time and effort to learn the keyboard layout.

Figure 1:
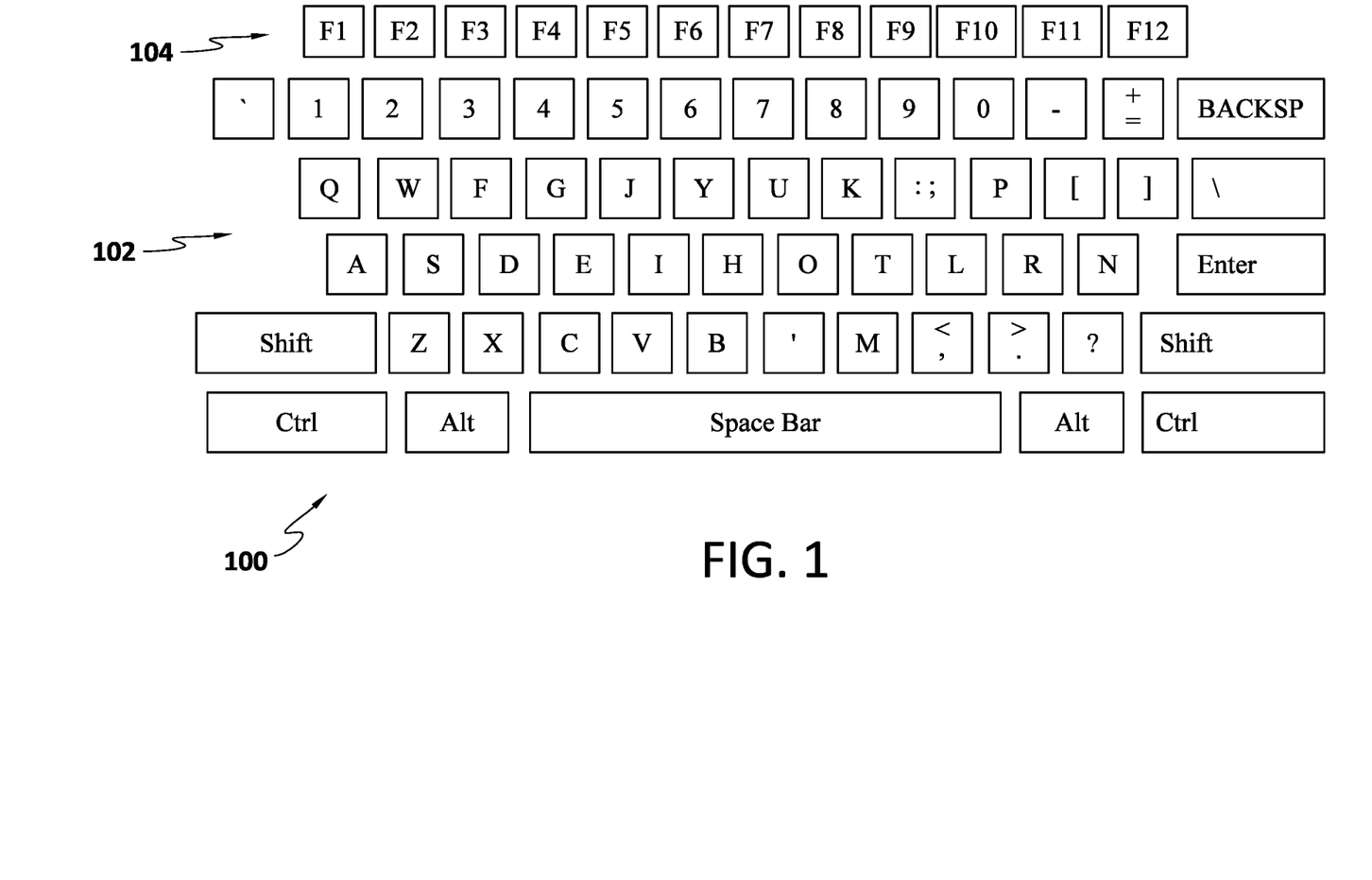
FIG. 1 illustrates a diagrammatic view of an embodiment of a powered communication system according to the present disclosure.

FIG. 1 shows a diagrammatic view of a powered communication device 100 according to a first embodiment of the disclosure. The powered communication device 100 advantageously comprises a keyboard layout 102 that rearranges keys to facilitate reduced finger movement. In particular, the keyboard layout 102 can arrange all or a substantial entirety of "the ordinals" along the center row of a keyboard, while retaining a majority or a substantial plurality of keys in the QWERTY layout to reduce the amount of time required for a user to learn to use the keyboard layout 102. The keyboard layout 102 can be arranged in embodiments as follows: from left to right, a home row comprises "a", "s", "d", "e", "i", "h", "o", "t", "l", "r", "n"; an upper row comprises "q", "w", "f", "g", "j", "y", "u", "k", "; (semi-colon)", "p"; and a bottom row comprises "z", "x", "c", "v", "b", "' (apostrophe)", "m", ", (comma)", ". (period)".

When using the QWERTY layout as designed (left pinky finger on "a", left ring finger on "s", left middle finger on "d", left index finger on "f", right index finger on "j", right middle finger on "k", right ring finger on "l", and right pinky finger on ";"), typing the ordinals results in seven occurrences of the fingers flexing while extended beyond their initial placement. This occurs with the left middle finger (once—"e"), left index finger (twice—"r" and "t"), right index finger (twice—"h" and "n"), right middle finger (once—"l"), and right ring finger (once—"o").

When using the improved powered communication device 100 of the disclosure, however, as designed (left pinky finger on "a", left ring finger on "s", left middle finger on "d", left index finger on "e", right index finger on "o", right middle finger on "t", right ring finger on "l", and right pinky finger on "r"), typing the ordinals results in three occurrences of the fingers flexing while extended beyond their initial placement. This occurs with the left index finger (once—"i"), right index finger (once—"h"), and right pinky finger (once—"n").

In comparing these two layouts of typed communication regarding the eleven most used words in the English language, the improved powered communication device 100 of the disclosure decreases finger flexion and extension by over half, a noticeable and significant improvement for those physically impaired by the symptoms of CTS. These impaired individuals using this improved powered communication device 100 are able to engage in typed communication with less pain and discomfort for longer periods of time.

In the preferred embodiment, the keys of the improved powered communication device are chosen to share the same key locations with the QWERTY layout while still maintaining the benefits of the more easily accessible characters the ordinals. This means that there are a total of eighteen keys sharing the same location when comparing the QWERTY layout and the layout 102 (five on the home row, five on the upper row, and eight on the bottom row), with the rest of the keys being selected to reduce movement of the fingers. In this embodiment, the lesser-used letter keys (the letters that are not in the ordinals) are placed in the same location as they are found in the QWERTY layout's upper and lower rows when possible.

This allows for a greater ease of learning and usage for those already accustomed to the QWERTY layout while facilitating reduction of finger flexion and extension and the subsequent CTS symptoms.

It will be understood that the disclosed layout 102 is merely exemplary, and that other layouts of the keys that fall within the spirit and scope of the disclosure are also contemplated. For example, the ordinals may be alternatively arranged on the home row or in suitable locations in the top and bottom rows depending on a particular application or a particular user's needs. In other embodiments, the home row may have more than five letters in common with the QWERTY home row layout to account for those users afflicted by the symptoms of CTS that have extreme difficulty changing usage from the QWERTY layout. In these embodiments, the upper and lower rows share the same letter key locations as the QWERTY layout when possible. In embodiments, the bottom row may have at least four of the least-used letters of the alphabet and the upper row may have at least three of the least-used letters of the alphabet.

The powered communication device 100 can further comprise customizable function keys 104 along a conventional location. The customizable function keys 104 can advantageously be manually or automatically customized to further reduce a user's finger movements. In embodiments, a user may specify that each key of the function keys 104 corresponds to a commonly used and/or arduous-to-type word. By customizing the function keys 104 to correspond to such words, the user may simply strike the desired one of the function keys 104 rather than typing out each letter of the desired word.

In embodiments wherein the customizable function keys 104 are manually customized, the user may cooperate with an interface of a computer system associated with the powered communication device 100 (discussed below) in order to set or reset the function keys 104 to the desired words. In embodiments wherein the customizable function keys 104 are automatically customized, a processor of the computer system associated with the powered communication device 100 may determine based on use metrics certain words that may be advantageously set to one of the customizable function keys 104 in order to further reduce finger movement.

For example, the processor of the computer system may cooperate with a storage of the computer system to assess, based on the user's history of typed words, which words occur most frequently (which can be a function of the user's occupation), which words require the most finger movement, and/or which words take the most time to type (in part because of the user's determined propensity for misspelling the word and thus having to delete letters and retype the word). The processor can accordingly determine which words can most reduce finger movement by being keyed to one of the function keys 104. The processor of the computer system may cooperate with an artificial intelligence modality such as a machine learning model to make the determination of what words from the user's repertoire are most suitable for the customizable function keys 104.

For example, the machine learning model may be trained according to a standard set of typing samples that the user performs when first using the powered communication device 100 or when activating the automatic customization of the function keys 104, according to exemplary preexisting writing samples (such as a number of sent emails, word documents, social media posts, or other preexisting writing samples), or according to a set of standard samples pertaining to a particular occupation or use of the powered communication device 100. For instance, the user may select a pre-determined customization of the function keys 104 corresponding to legal writing, scientific writing, engineering writing, journalistic writing, pedagogical writing, musical writing, political writing, a combination thereof, or any other suitable field.

The processor may further determine the best arrangement of the customized keys based on, for example, the user's patterns of typing. In certain embodiments, the processor may determine that the most commonly used words that are customized or keyed to the function keys 104 may be placed near the user's index fingers, e.g. at f5 or f7, to further minimize movement of the fingers. This may be particularly advantageous if the user's patterns of typing indicate that the user utilizes the index fingers more than the other fingers. It will be understood that the above description is merely exemplary, and other arrangements and methods are contemplated by the present disclosure.

By arranging the keyboard layout 102 as shown in FIG. 1, the user may advantageously avoid, treat, or mitigate symptoms of various pathologies including the symptoms of CTS, as the amount of movement required of the user's fingers and hands is reduced. By reducing such movement, especially when considered over the extreme amounts of time that most users spend typing at a computer in their jobs as well as at leisure, the numerous and significant adverse effects of the symptoms of CTS and other overuse pathologies are addressed. This leads to improved well-being for a user as pain, tingling, and numbness in the hands and fingers are reduced, the user is better able to participate normally in daily activities, and overall dexterity with the hands is improved. Other pathologies that may be alleviated or treated using the powered communication device 100 of the disclosure include, but are not limited to, tendinitis, De Quervain's Tenosynovitis, Stenosing Tenosynovitis, Capsulitis, and muscle or tendon strain.

Figure 2:
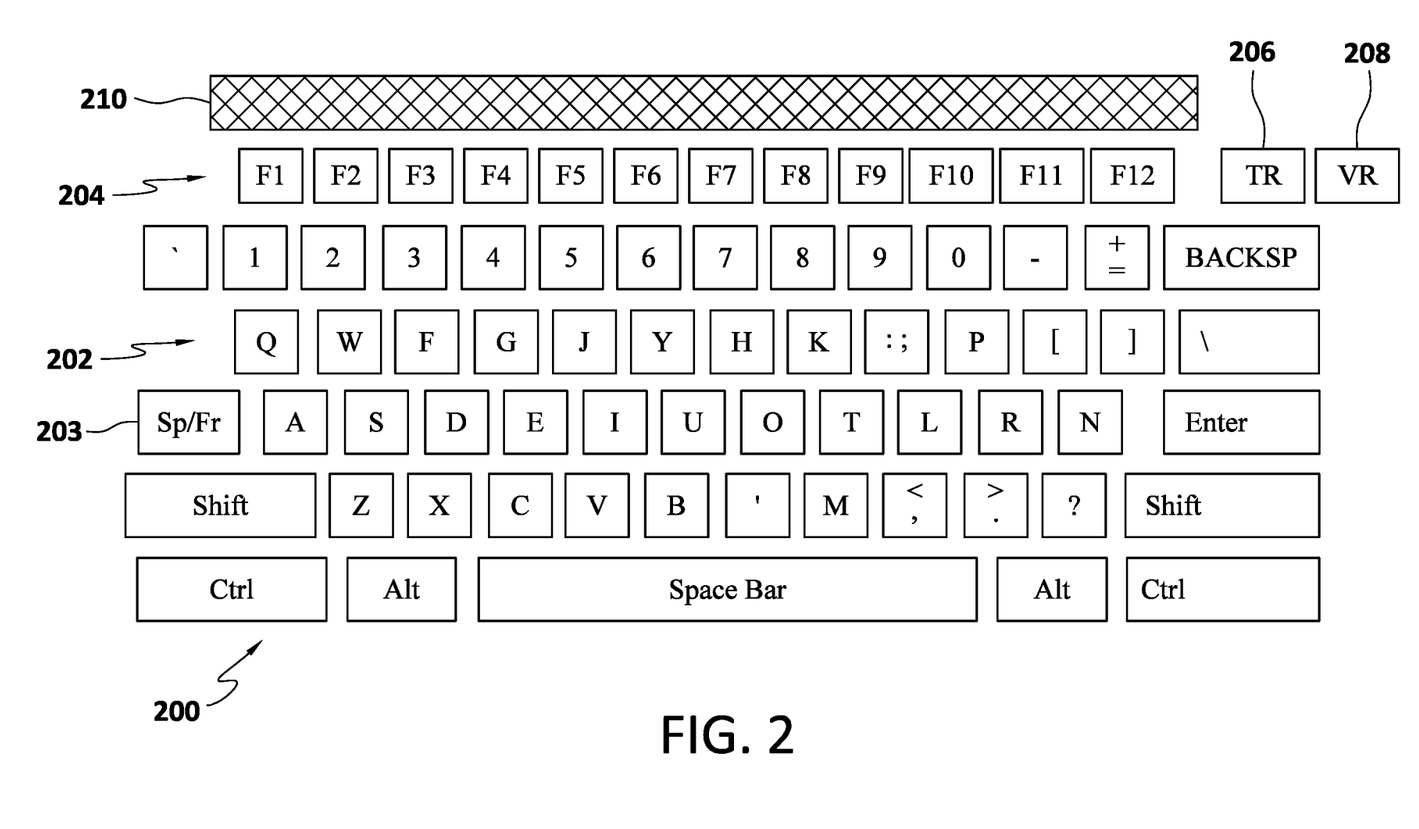
FIG. 2 illustrates a diagrammatic view of an embodiment of a powered communication system according to another embodiment of the present disclosure.

FIG. 2 illustrates an embodiment of a powered communication device 200 comprising an improved layout 202 of keys that facilitate a reduction in finger movement and thereby a delay, treatment, and/or mitigation of the symptoms of CTS and other pathologies. The layout 202 is configured in particular for users typing in Spanish or French. As Spanish and French make greater use of the letter "u" than English, the letter "u" may be relocated to a central position on the home row, replacing "h", which is correspondingly replaced to the upper or top row. The layout 202 may be provided as the default setting for a powered communication device 200 according to embodiments of the disclosure, or may be a setting to which a user can switch either automatically or manually.

That is, the default setting may be the layout 102 described in regards to the embodiment of FIG. 1, but the user may switch the layout 102 to the layout 202 if the user switches to typing in French or Spanish. The switch to the layout 202 may be effected through an operating system of a personal computer with which the powered communication device is configured to cooperate, or may be effected through a key 203 that toggles between the layouts 102, 202.

As with the benefits realized through use of the powered communication device 100 as described above, the use of the powered communication device 202, in particular for users typing in Spanish or French, effectively treats, delays, or mitigates the symptoms of CTS and other pathologies, relieving the user of pain, tingling, numbness, discomfort, and inconvenience associated with the resulting impairment in daily tasks.

The powered communication device 200 may also comprise customizable function keys 204 ranging from f1-f12 as described above, and which may serve analogous functions. Additionally, the customizable function keys 204 can have a set of customized words which each of the customizable function keys 204 represent, with a first set of customized words pertaining to a default layout such as layout 102 and a second distinct set of customized words pertaining to a second layout such as layout 202. A user may thus have a particular set of words shortcutted by the customizable function keys 204 when typing in English and a distinct set of words shortcutted by the customizable function keys when typing in Spanish or French, for example.

The powered communication device comprises additional features such as solar-power module 210 and text recognition key 206 and voice recognition key 208. The solar-power module 210 may advantageously provide independent power to the powered communication device 200 externally of a personal or other computing device to which the powered communication device 200 may be cooperating.

Not shown is a power storage unit such as a rechargeable battery embedded within a body of the powered communication device 200 which is configured to store the power generated at the solar-power module 210 for use when power from an external source is unreliable or absent. It will be understood that the depicted arrangement of the solar-power module 210 is merely exemplary, and the solar-power module 210 may be located in any suitable location and have any suitable configuration (including comprising multiple distinct solar-power modules) located at various locations on the powered communication device 200.

The text recognition key 206 and the voice recognition key 208 may advantageously allow a user to quickly and easily toggle between text recognition and voice recognition modes of operation, such that when one or the other of the keys 206, 208 is pressed, the powered communication device 200 and/or a computing system with which the powered communication device 200 cooperates may enter a text recognition mode to track the user's typing. This may be beneficial for learning the user's typing patterns and automatically adjusting the operation of the powered communication device 200 accordingly, such as the words associated with the customizable function keys 204. Likewise the voice recognition mode may activate a microphone (not shown) embedded in either or both of the powered communication device 200 and the computing device with which the powered communication device 200 cooperates to record a user's speech for subsequent natural-language processing.

Figure 3:
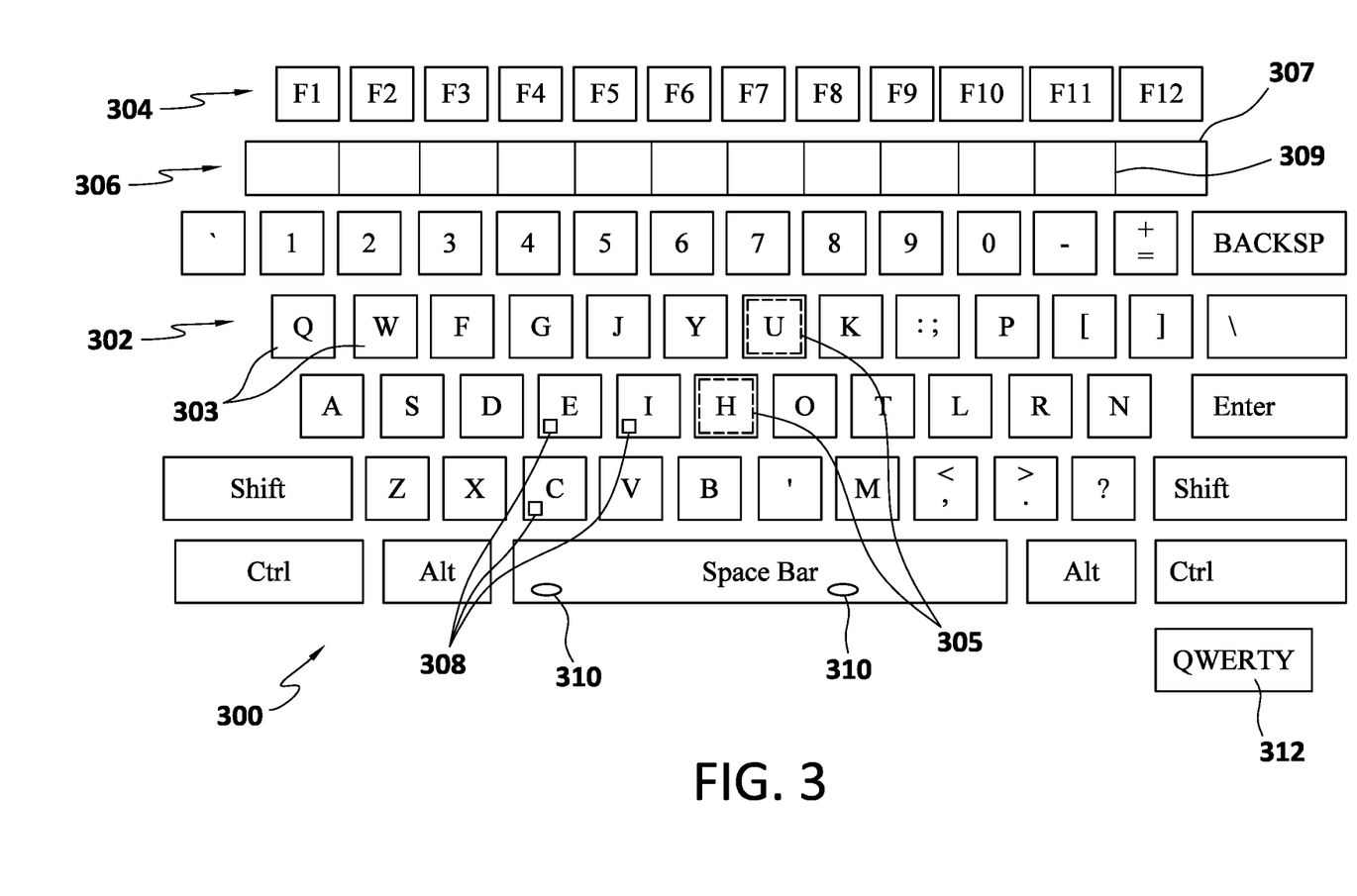
FIG. 3 illustrates a diagrammatic view of an embodiment of a powered communication system according to another embodiment of the present disclosure.

FIG. 3 depicts another embodiment of a powered communication device 300 according to the disclosure. The powered communication device 300, as with the foregoing embodiments, may comprise an advantageous layout 302 that rearranges the ordinals to a location on the layout that reduces the amount of finger movement required for typing, thereby treating, delaying, and/or mitigating the symptoms of CTS and other pathologies, while not making the new layout so different from the well-known QWERTY layout that users struggle to relearn the new layout 304. The powered communication device 304 further comprises a display 306 configured to indicate to a user which customized words correspond to each one of a set of customizable function keys 304, which in the depicted embodiment range from f1-f12.

The display 306 may comprise dividing portions 309 that discretize an area defined by a border portion 307, such as a bevel, making the words displayed on the display 306 easy to attribute to the corresponding one of the customizable function keys 304. In the embodiment of FIG. 3, the display 306 is arranged adjacent to and below the customizable function keys 304. The display 306 may be or comprise a liquid crystal display (LCD), an in-plane switching liquid crystal display (IPS-LCD), a light emitting diode (LED) and variants thereof, plasma, quantum dot, electroluminescent display, or any other suitable display. The display 306 can be in communication with a processor of a computing system as described hereafter to update the display 306 with the user's current set of customizable function keys 304, which as discussed above may vary depending on the layout 102, 202, 302 and may be dynamic based on the user's current needs.

One or more keys 303 of the layout 302 may be provided with one or more of an individual display 305 configured to indicate to a user what letter or character the key represents at a particular time, a temperature sensor 308, and/or a sensor 310 configured to detect a user's pulse. Each of the individual display 305, the temperature sensor 308, and the sensor 310 may be embedded in the individual keys 303. The individual display 305, temperature sensor 308 and sensor 310 may all be in communication with a processor of the computing system described in greater detail hereafter. The individual display 305 may be or comprise similar displays as described above in regards to the display 306.

In embodiments, the powered communication device 300 may comprise or be configured to cooperate with a projecting device (not shown) that displays on a surface of the individual keys 303 an indicium that shows a user what character is associated with each one of the individual keys 303. The projecting device may be configured to communicate with the powered communication device 300 to modulate the indicium at necessary to, for example, suggest a predicted key 303 that should be struck next, or to highlight those keys that have changed when toggling between, for example, the QWERTY layout and the layout 302. It will be understood that the indicium can take any suitable form, size, shape, color, frequency, or other characteristic.

In view of the ability of the powered communication device 300 to switch or toggle between different layouts, the individual display 305 on one or more of the keys 303 may correspondingly switch to indicate what the current layout of the powered communication device 300 is. For example, if the user switches from an English-based layout 102, 302 to a Spanish- or French-based layout 202, the individual display 305 on letters "h" and "u" may indicate to the user the different arrangement of the letters corresponding to English or Spanish/French, as "h" and "u" switch between the layouts 102, 302, 202. The powered communication device 300 is further able to toggle between a QWERTY layout, a Dvorak layout, a Colemak layout, a layout 102, 202, 302 according to embodiments of the disclosure, or any other suitable layout based on a particular user's needs. For example, certain workstations at libraries, schools, and workplaces are configured for use by different people throughout the day. A powered communication device 100, 200, 300 according to the disclosure advantageously can toggle between different layouts to accommodate such different users at different times.

The powered communication device 300 may advantageously track a user's health and predict the onset of symptoms of CTS and other pathologies through the use of the sensors 308, 310, as well as through assessing the patterns of typing recorded through use of the layout 302 generally. In embodiments, the sensors 308, 310, which are in communication with the processor of a computing system, may indicate the temperature and a pulse of a particular user. The processor of the computing system may determine that a progressively rising temperature and/or pulse correspond to an onset of CTS symptoms. The powered communication device 300 may be provided with means such as vibration means, display means, noise-producing means, or other utilities (not shown) for indicating to a user that CTS symptoms are or shortly will be setting in and that the user should take a short break or cease from typing for the remainder of the day, for example.

In embodiments, the sensors 310 may be placed at or in the space bar for assessing a user's pulse, as the thumbs tend to spend more time proximate the space bar than do the fingers at any one key, thereby facilitating a more accurate reading. The temperature sensors 308 may be disposed on one or more, including an entirety, of the keys 303, serving to collect temperature-related information from individual fingers. It will be appreciated that the depicted embodiment is merely exemplary, and the sensors 308, 310 may be disposed on any suitable key or location. The sensors 310 for detecting a user's pulse may be pressure sensors, optical sensors, or any other suitable sensor for detecting a pulse. The sensors 308 for determining temperature may be or include infrared sensors, thermocouples, thermistors, semiconductor-based sensors, combinations thereof, or any other suitable type of sensor. Additional sensors are contemplated as part of the disclosure, and are not limited to temperature and pulse.

Figure 4:
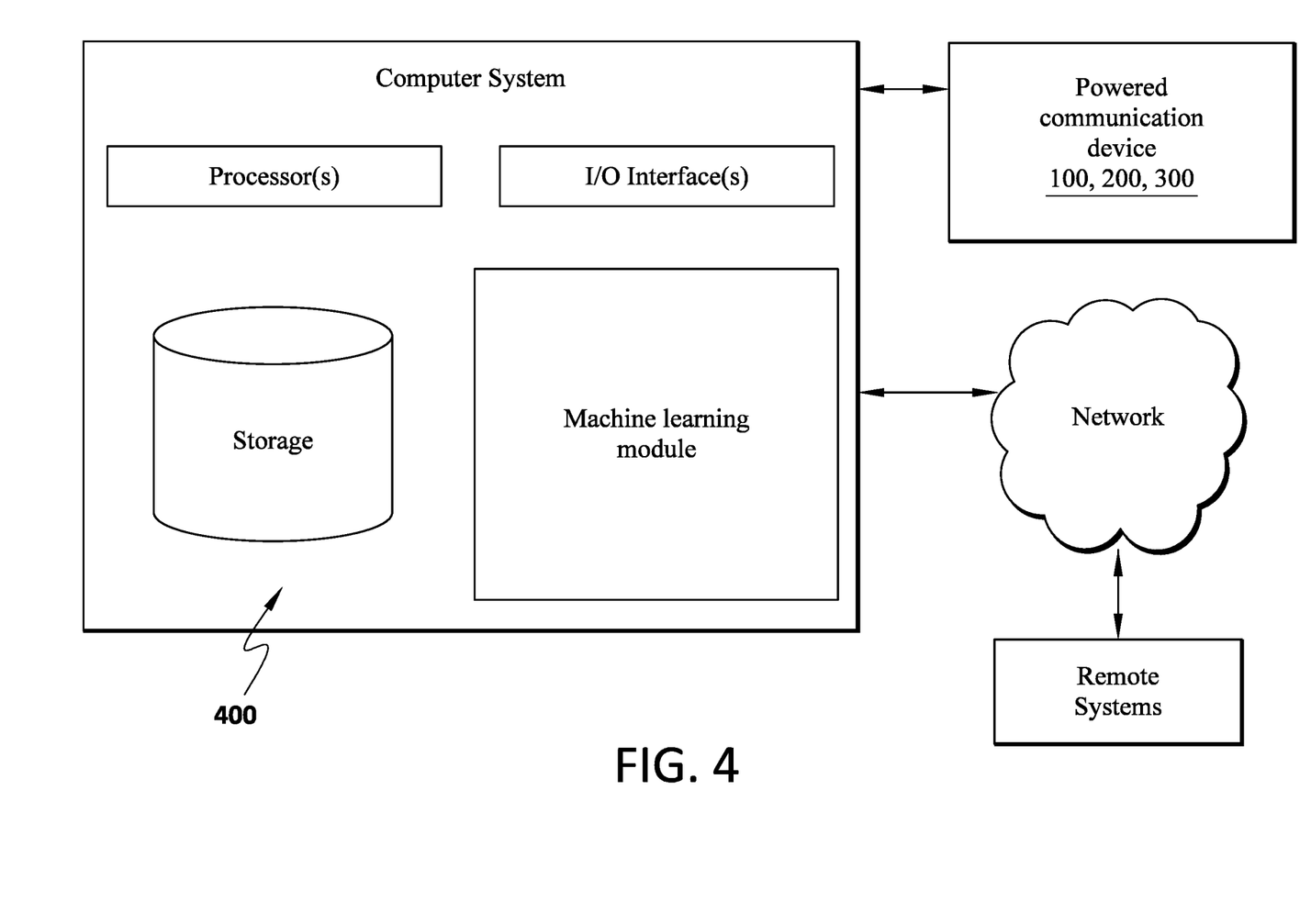
FIG. 4 illustrates a computer system comprising at least one processor configured to receive information from a powered communication device according to embodiments of the disclosure.

FIG. 4 depicts a computer system 400 configured to cooperate with a powered communication device 100, 200, 300 according to embodiments of the disclosure. The computer system 400 may comprise storage, processor(s), I/O interfaces, and artificial intelligence engines such as machine learning models according to embodiments. The computer system 400 may comprise input or output hardware in addition an interface through which a user may provide information, such as the powered communication device 100, 200, 300 and associated sensors 308, 310.

The computer system 400 may be embedded in or connected to the powered communication device 100, 200, 300, may be associated with a computer with which the powered communication device 100, 200, 300 cooperates, or may be remote from the powered communication device 100, 200, 300 and configured to communicate with the powered communication device remotely.

In turn, the computer system 400 can be configured to provide indicia or to otherwise prompt a user to adjust usage of the powered communication device 100, 200, 300 to delay the onset of, treat, or mitigate symptoms of CTS and for improved use of the powered communication device 100, 200, 300, such as through displays 306, 303. The computer system 400 may be connected through a network to remote systems on which the embodiments may further be housed and performed.

The processor of the computer system 400, as described above, may be configured to receive data from the sensors 308, 310 to monitor the health of a user, in particular the onset of CTS symptoms. The processor may track the user's pulse and heartrate throughout the course of one typing session, multiple subsequent typing sessions, and over the user's history of using the powered communication device 100, 200, 300. The user's pulse and heartrate, as well as information related to speed, accuracy, and other types of patterns when typing (such as particular word choice), can be uploaded to an artificial intelligence engine or module such as a machine learning model.

The machine learning model can be configured to ascertain commonly used words, commonly misspelled or mistyped words, and words that require undue finger movement. The machine learning model can suggest or automatically populate the customizable function keys of any of the foregoing embodiments with words determined to impose unnecessary stress on a user's fingers, hands, and arms, so that the customizable function keys can replace the effort of typing out each individual letter for said words.

To predict which words may impose the most unnecessary stress on a user's hands, the machine learning model may be trained with a sample of the user's writing, such as from professional settings (work deliverables), school settings (essays and term papers), or social media posts (such as comments made on online forums), to assess the user's word choices. The machine learning model may also be trained by a calibration procedure requiring the user to type a predetermined sequence of words to ascertain the user's typing patterns, e.g. time between key strikes of particular keys, temperature, pulse, typos, and etc.

The machine learning model may be, but is not limited to, an artificial neural network, and may draw connections between input values relating to a user's typing patterns (including words used, typing speed, typos, etc.) and health values (such as from the temperature and pulse sensors 308, 310). The machine learning model is configured to convert the above input values and the connections between them into predictions regarding the onset of symptoms of CTS, including a predicted timeframe of onset of symptoms.

In an embodiment, the user may be required to type on the powered communication device a well-known passage from a famous speech, e.g. the Gettysburg Address, or a common document such as the text of a Dr. Seuss book or a Charles Dickens novel. The machine learning model may ascertain certain patterns of use based on such a calibration procedure as well as through continued monitoring of the user's typing patterns and health indicators.

The machine learning model can further be configured to determine patterns of health-related indicia such as pulse and temperature related to particular typing trends. For example, the machine learning model can assess that a particular user experiences an increase in temperature and pulse, and a corresponding decrease in typing accuracy and speed, in the minutes and hours leading up to the acute onset of CTS symptoms. The processor is configured to, upon such determination from the machine learning model, indicate to a user that usage of the powered communication device 100, 200, 300 should be adjusted. As described above, the processor of the computer system 400 may activate vibration means, display means, noise-producing means, or other devices to provide indicia to a user to take a break or discontinue use of the powered communication device.

In an embodiment, the display 306 of the powered communication device 300 can be configured to cooperate with the processor of the computer system 400 to provide messages to a user. For instance, the display 306 may provide instructions such as "Give your hands a 5 minute break," or "Finish this task tomorrow after your hands have had a chance to rest." In other embodiments, the powered communication device 300 is configured to stop responding entirely to keystrikes by the user for a time to provide the user with a mandatory break of, for example, five to ten minutes.

The computer system 400 may further be configured to cooperate with multiple devices to compile information about a user; for example, the user may utilize a powered communication device 100, 200, 300 according to embodiments of the disclosure at work and at home. The multiple communication devices 100, 200, 300 may be connected through a network, thereby improving the ability of the computer system 400 to assess a user's typing and health patterns. The computer system 400 may further be in communication with a user's smart devices to assess the user's typing patterns on the QWERTY keyboards thereon.

In embodiments, the layout 102, 202, 302 may be provided in electronic format for use on smart devices such as tablets, phones, and other devices utilizing touch screens. It will be appreciated that the layouts 102, 202, 302 may be embedded within an operating system for a computer such that the layouts 102, 202, 302 are an available configuration for any user and compatible with the operating system of whatever computing device the powered communication device 100, 200, 300 cooperates with.

A method of automatically determining the customizable function keys of the powered communication device embodiments 100, 200, 300 disclosed herein may comprise the steps of:
 providing a powered communication device having an improved layout of keys configured to treat, delay, and/or mitigate the onset of symptoms of CTS;
 monitoring a user's typing on the powered communication device;
 determining a subset of words most commonly typed by the user;
 identifying a second subset of words from the subset of words most commonly typed by the user, the second subset comprising words requiring finger movement in excess of the finger movement required for the remainder of the subset of words;

assigning each word of the second subset of words to one of a plurality of customizable function keys of the powered communication device;

and optionally displaying each word of the second subset words using a display on the powered communication device.

The above method may optionally comprise the further step of determining from the first or second subset of words a third subset of words most commonly mistyped or misspelled by the user.

A method of monitoring the health of a user using the powered communication device according to embodiments of the disclosure may comprise the steps of:

providing a powered communication device having an improved layout of keys configured to treat, delay, and/or mitigate the onset of symptoms of CTS;

providing a computing system comprising at least one processor;

monitoring at least one indicium of a user's health using at least one sensor embedded in the powered communication device and in communication with the at least one processor;

determining in the processor from the at least one indicium of the user's health an onset of CTS symptoms;

and optionally indicating to the user that CTS symptoms are impending.

By providing a powered communication device for treatment of carpal tunnel syndrome and other pathologies and methods for using the same according to the disclosed embodiments, the problems of existing keyboards such as QWERTY, Dvorak, and Colemak requiring excessive finger movement and/or being too different from known layouts to feasibly be adopted by the market are addressed. The powered communication device embodiments of the present disclosure advantageously retain a significant portion of the QWERTY keyboard layout while arranging the most-used letters of the alphabet along a home or center row to minimize finger movement and thereby treat, mitigate, or delay the onset of symptoms of CTS. The powered communication device further comprises customizable function keys that further minimize the amount of finger movement during typing, and may comprise at least one sensor configured to monitor the health of a user.

While the disclosure discusses embodiments for a keyboard, powered communication device embodiments of the disclosure may be used with other devices.

Not necessarily all such objects or advantages may be achieved under any embodiment of the disclosure. Those skilled in the art will recognize that the disclosure may be embodied or carried out to achieve or optimize one advantage or group of advantages as taught without achieving other objects or advantages as taught or suggested.

The skilled artisan will recognize the interchangeability of various components from different embodiments described. Besides the variations described, other known equivalents for each feature can be mixed and matched by one of ordinary skill in this art to construct a communication device under principles of the present disclosure. Therefore, the embodiments described may be adapted to communication systems adapted for use in smart devices, non-personal computers, and other settings as well.

Although a powered communication device has been disclosed in certain preferred embodiments and examples, it therefore will be understood by those skilled in the art that the present disclosure extends beyond the disclosed embodiments to other alternative embodiments and/or uses of the disclosure and obvious modifications and equivalents. It is intended that the scope of the present disclosure disclosed should not be limited by the disclosed embodiments described above but should be determined only by a fair reading of the claims that follow.

The invention claimed is:

1. A powered communication device for treatment, mitigation, and/or delay of symptoms of carpal tunnel syndrome, the powered communication device comprising:

a keyboard comprising a set of keys arranged to minimize the amount of finger movement required of a user during typing, the set of keys divided into a top row, a home row, and a bottom row;

the top row comprising the letters "q", "w", "f", "g", "j", "y", "u", "k", "; (semi-colon)", "p";

the home row comprising the letters "a", "s", "d", "e", "i", "h", "o", "t", "1", "r", "n";

the bottom row comprising the letters "z", "x", "c", "v", "b", "' (apostrophe)", "m", ", (comma)", ". (period)";

at least one first sensor embedded in at least one key of the keyboard and connected to a processor in communication with the powered communication device; and at least a second sensor embedded in at least one key of the keyboard and connected to the processor in communication with the powered communication device;

wherein the processor is configured to determine an onset of symptoms of CTS from first and second signals obtained from the at least one sensor and at least one second sensor.

2. The powered communication device of claim 1, further comprising a set of customizable keys.

3. The powered communication device of claim 2, wherein the set of customizable keys is functions keys f1-f12.

4. The powered communication device of claim 2, wherein the set of customizable keys are configured to be customized to key for a desired subset of words.

5. The powered communication device of claim 4, wherein the set of customizable keys is configured such that the desired subset of words is determined manually by a user.

6. The powered communication device of claim 4, wherein the set of customizable keys is configured such that the desired subset of words is determined automatically by a processor in communication with the powered communication device.

7. The powered communication device of claim 4, further comprising at least one display configured to indicate to a user the desired subset of words corresponding to each key of the set of customizable keys.

8. The powered communication device of claim 1, further comprising a solar-power module and at least one power storage unit.

9. The powered communication device of claim 1, wherein the at least one sensor is configured to derive at least one health indicium of the user.

10. The powered communication device of claim 1, wherein the powered communication device is configured to indicate to the user that CTS symptoms are imminent by providing an indicium on a display.

11. The powered communication device of claim 1, wherein the powered communication device is configured to prevent the user from striking any of the keys after the processor determines that CTS symptoms are imminent.

12. A powered communication device for treatment, mitigation, and/or delay of symptoms of carpal tunnel syndrome in users typing in Spanish or French, the powered communication device comprising:

a keyboard comprising a set of keys arranged to minimize the amount of finger movement required of a user during typing, the set of keys divided into a top row, a home row, and a bottom row;

the top row comprising the letters "q", "w", "f", "g", "j", "y", "h", "k", "; (semi-colon)", "p";

the home row comprising the letters "a", "s", "d", "e", "i", "u", "o", "t", "l", "r", "n";

bottom row comprising the letters "z", "x", "c", "v", "b", "' (apostrophe)", "m", ", (comma)", ". (period)";

at least one first sensor embedded in at least one key of the keyboard and connected to a processor in communication with the powered communication device; and at least a second sensor embedded in at least one key of the keyboard and connected to the processor in communication with the powered communication device;

wherein the processor is configured to determine an onset of symptoms of CTS from first and second signals obtained from the at least one sensor and at least one second sensor.

13. The powered communication device of claim 12, wherein the powered communication device 16 is configured to switch between an English configuration in which "h" is on the home row and "u" is on the top row, and a Spanish/French configuration in which "h" is on the top row and "u" is on the middle row.

14. The powered communication device of claim 13, further comprising a key for switching between the English configuration and the Spanish/French configuration.

* * * * *